United States Patent [19]

Tapin

[11] Patent Number: 4,952,398

[45] Date of Patent: Aug. 28, 1990

[54] BIOCIDAL COMPOSITION WITH COPPER ALGICIDE

[76] Inventor: Jean Tapin, 06550 LaRoquette, 770 Av. de La Republique, 1 Domaine Des Lauriers Roses, France

[21] Appl. No.: 169,378

[22] Filed: Mar. 17, 1988

[51] Int. Cl.$^5$ ............................................. A01N 61/02
[52] U.S. Cl. ................................................ 71/67; 71/3; 71/4; 424/630; 514/642; 514/643
[58] Field of Search ................... 424/141, 143; 71/3, 71/4

[56] References Cited

U.S. PATENT DOCUMENTS

| | | | |
|---|---|---|---|
| 2,506,635 | 5/1950 | Flenner | 424/163 X |
| 2,581,951 | 1/1952 | Harshaw et al. | 424/143 |
| 2,772,199 | 11/1956 | Zakheim | 424/143 X |
| 2,938,830 | 5/1960 | Davey et al. | 424/141 |
| 2,952,581 | 9/1960 | Wright | 424/141 X |
| 3,003,913 | 10/1961 | Rowe | 424/163 |
| 3,292,069 | 1/1967 | Kowalski | 424/143 |
| 3,681,492 | 8/1972 | Kotzbauer | 424/143 X |
| 4,193,993 | 3/1980 | Hilditch | 424/141 X |
| 4,436,744 | 3/1984 | Harr | 424/143 X |
| 4,698,334 | 10/1987 | Horriere et al. | 424/143 X |

FOREIGN PATENT DOCUMENTS 0395259 11/1973 U.S.S.R. ............................ 424/143

Primary Examiner—Thurman K. Page
Attorney, Agent, or Firm—Hurt, Richardson, Garner, Todd & Cadenhead

[57] ABSTRACT

The present invention is directed to an improved chemical composition for the treatment of water which is particularly adapted to provide increased biocide activity. By biocide is meant in particular an algacide, a bactericide and a fungicide. The composition is also suitable for the disinfection of animal breeding places an the cleansing of soil.

28 Claims, 2 Drawing Sheets 1) 715 kg SOL. $CO_3Na_2$ 9.2%  
2) 565 kg SOL. $SO_4Cu$ 5.8%  
3) 200 LITERS $H_2O$

STIR
1

SETTLING
2

SIPHON
3

1300 LITERS $H_2O$

STIR
4

SETTLING
5

SIPHON
6

1300 LITERS $H_2O$

STIR
7

SETTLING
8

SIPHON
9

BIOCIDAL COMPOSITION WITH COPPER ALGICIDE

BACKGROUND OF THE INVENTION

1. Field of the Invention

The present invention is directed to an improved chemical composition for the treatment of water which is particularly adapted to provide increased biocide activity. By biocide is meant in particular an algacide, a bactericide and a fungicide. The composition is also suitable for the disinfection of animal breeding places and the cleansing of soil. Additionally, a flocculent can be added to create a composition having the dual activity of a biocide and a flocculent.

2. Description of the Prior Art

It is well known that ordinary water contains various types of micro-organisms, such as bacteria, algae, and fungi, which if left unchecked can multiply to the point of rendering the water unfit for human use. Over the years a number of different reagents or compounds have been proposed to control, if not eliminate, the growth of such micro-organisms in water. Early attempts to solve this problem have included the use of active chlorine, copper-containing compounds or quaternary ammonium salts. Active chlorine-containing compounds have been found to have a number of serious drawbacks including rapid decomposition, pungent odor and corrosive action of water handling systems.

Copper compounds, such as copper sulfate, copper carbonate and other related copper salts tend to exert algaecidic activity only at relatively high concentrations making use of such compounds expensive. Copper salts, such as copper sulfate, also have a tendency to precipitate from aqueous solutions containing carbonates and bicarbonates. U.S. Pat. No. 2,734,028 to Domogalla attempts to solve this problem of copper precipitation by the inclusion of an hydroxyamine, such as alkanolamine, as a solubilizing agent to maintain the copper cation in solution in a variety of hard water systems or in water having large amounts of dissolved carbon dioxide.

Quaternary ammonium compounds have also been proposed as algaecides and bactericides. Their bactericidal power has been attributed to the tensio-active effect and the formation of compounds between quaternary ammonium salts and proteins. These compounds, however, have been known to irritate human skin and to loose activity in the presence of hard, calcium-containing water. Stayner et al., U.S. Pat. No. 2,692,231, indicate that quaternary ammonium salts, such as alkyl dimethyl benzyl ammonium chlorides by themselves are inadequate under certain circumstances. Their attempted solution is to combine the quaternary ammonium salt with a nonanionic organic material having a solubility in water of less than about 5%. The nonanionic organic material is characterized as being hydrophobic-weakly hydrophilic species and as a promoter for the quaternary ammonium salt enhancing the microbicidal effect of the quaternary ammonium compound.

Darragh et al., U.S. Pat. No. 2,688,583, disclose that quaternary ammonium salts have the further drawback of producing a cloudy dispersion upon being added to water. Their solution to this problem is to include with the quaternary ammonium salt an inorganic water soluble aluminum salt capable of producing clear aqueous dispersions throughout a range of concentrations. Aluminum sulfate or aluminum chloride have been employed in this capacity.

Zsoldos et al., U.S. Pat. No. 3,702,298, have attempted to control the growth of micro-organisms in water by maintaining a highly oxidizing alkaline aqueous solution consisting of an oxidizer bank of a large excess of peroxy compounds in combination with copper or silver salts (such as nitrate or sulfate salts) acting as an in situ catalyst. Optionally, a chelating agent, such as sodium citrate or acetate, can be employed to prevent precipitation of the metal catalyst.

To the best of applicant's knowledge, none of the previous attempts to control the growth of micro-organisms in water have succeeded in providing a safe, efficient, cost effective, long lasting composition which provides exceptional biocide activity and which can additionally include a flocculent.

BRIEF SUMMARY OF THE INVENTION

It is, therefore, an object of the present invention to provide a composition which is safe, effective and long lasting for the control, if not elimination, of micro-organisms (algae, fungi and bacteria) in swimming pool water systems.

It is another object of the present invention to provide a long lasting composition for the control of micro-organisms (algae, fungi and bacteria) in water which requires a minimum level of effort in order to provide safe conditions for human use of swimming pool water.

It is yet another object of the present invention to provide a composition for the control of micro-organisms (algae, fungi and bacteria) in swimming pool water which provides a dual function of a biocide and a flocculent.

It is yet a further object of the present invention to provide a composition which works well as a disinfectant for animal breeding places and as a soil cleanser.

The above objects of the present invention are achieved by providing a novel composition comprising a quaternary ammonium compound and a copper salt compatible with the quaternary ammonium compound. The quaternary ammonium compound can be present in the range of about 10 g/l to about 250 g/l, and the copper salt can be present in the range of about 1 g/l to about 20 g/l. Additionally a flocculant compatible with both quaternary ammonium compound and the copper salt may be added to aid in the removal of particulate matter in the swimming pool water.

Other and further objects of the present invention will be apparent from the following detailed description of the present invention.

DETAILED DESCRIPTION OF THE INVENTION

Figure 1:
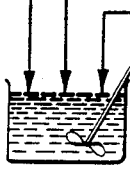
Figure 1:
Figure 1:
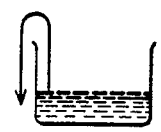
Figure 1:
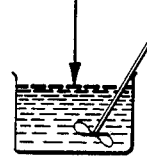
Figure 1:
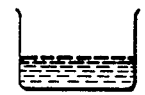
Figure 1:
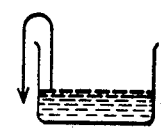
Figure 1:
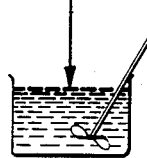
Figure 1:
Figure 1:
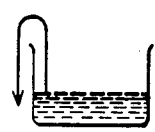
Figure 1:
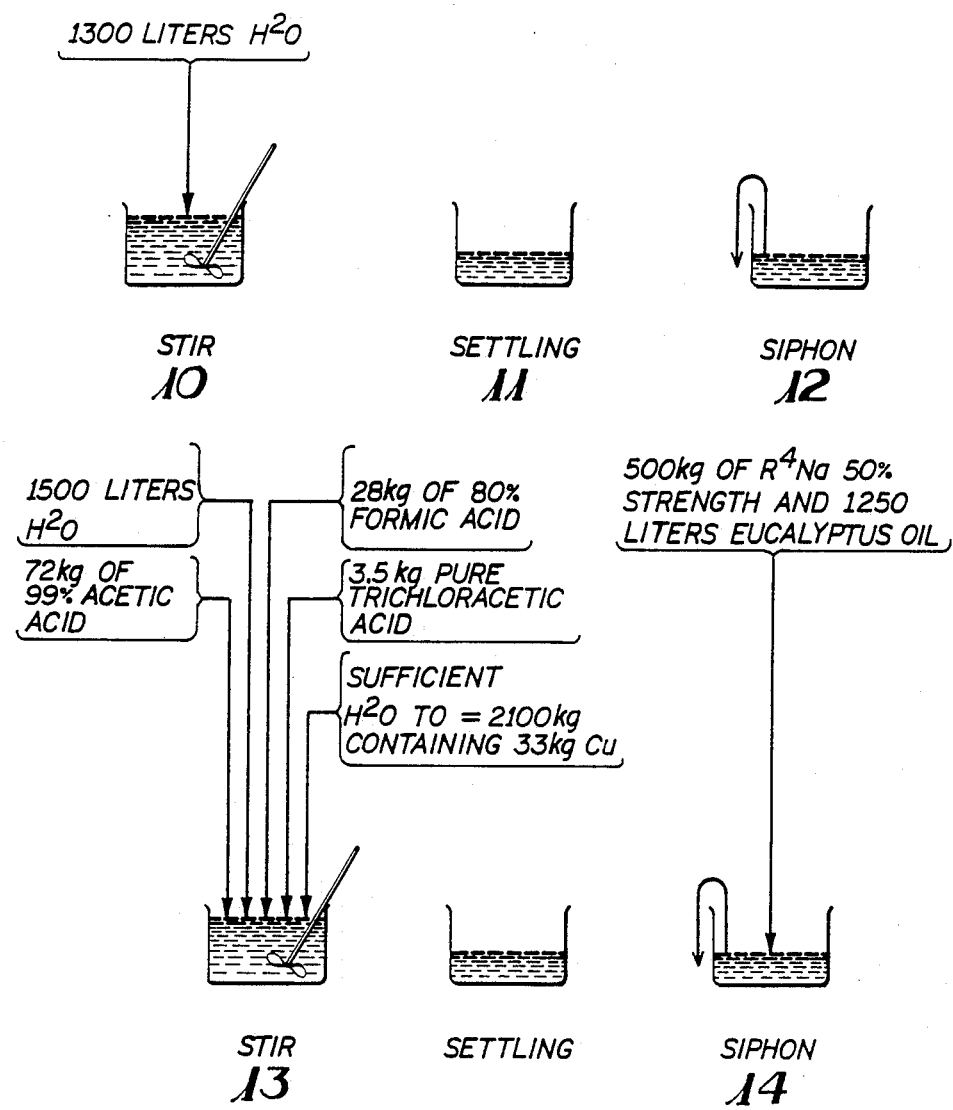

The novel composition of the present invention includes the combination of the biocide activity of quaternary ammonium compounds with that of copper salts. Applicant has discovered that by combining two such compounds the biocide activity level of the combination exceeds the sum of activity of the two compounds separately. For example, by combining a dose of 4 to 5 PPM of a quaternary ammonium compound with a corresponding dose of 0.7 to 0.9 PPM of copper, a result, at least equal to, and longer lasting than, the result of 15 to 20 PPM of the same quaternary ammonium compound alone can be obtained over the same period of time.

Suitable quaternary ammonium compounds for use in the biocidal composition of the present invention include chlorides or bromides of the following structures:

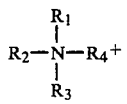

where $R_1$ is a long chain ($C_8$–$C_{20}$) aliphatic hydrocarbon and $R_2$, $R_3$ and $R_4$ are selected from the group consisting of methyl, ethyl, n-propyl, benzyl, and combinations thereof; amphoteric compounds where $R_1$ is a long chain ($C_8$–$C_{20}$) aliphatic hydrocarbon, $R_2$ is either —$CH_2CO_2$, or —$CH_2$—$CH_2$—$CO_2$, and $R_3$ and $R_4$ are selected from the group consisting of methyl, ethyl, n-propyl, benzyl, and combinations thereof. More than one such quaternary ammonium compound may be employed in the biocide composition. These quaternary ammonium compounds are generally available in the form of a mixture of quaternary ammonium salts of a homologous series which mixture will be referred to herein as a system.

The preferred quaternary ammonium system is one that has the strongest biocidal acitvity which has been approved by the appropriate governmental agency for its intended use. A chloride of alkyl dimethyl benzyl ammonium, of the formula

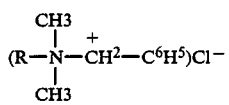

in which the radical alkyl comes from coco-nut oil seems to work best. THe division of the chain of fats of that ammonium chloride is the following:
$C_8$:3%; $C_{10}$:6%; $C_{12}$:56%; $C_{14}$:18%; $C_{16}$:10%; $C_{18}$ (stearyl):2%; $C_{18}$=oleyl 5%.

Specific quaternary ammonium systems which may be employed include quaternary ammonium bromides or derivatives of dibenzyl or tribenzyl ammonium, or alkyl radicals with different chain lengths or dialkyl benzyl ammonium chlorides, or alkyl bis-(ethoxyhydroxyethyl) benzyl ammonium chlorides, as well as amphoteric products such as propionic N-alkylamino acid, and propionic diamine N-alkyl propylene acid, having bactericidal properties. Of course, it is preferrable that the selected quaternary ammonium system is one that has been approved by the appropriate governmental agency.

The copper salts which can be used in the present composition are: chlorides, bromides, sulfates, acetates, formates, trichloroacetates, or salts of other organic acids, other solubilizing anions compatible with the selected quaternary ammonium systems, and combinations of such salts. The preferred copper salts are combinations of acetates, formates and trichloroacetates.

In the composition of the present invention in aqueous form, the quaternary ammonium compound or system can be present in the range of about 10 g/l to about 250 g/l, with about 32 g/l being preferred. The copper salts can be present in the range of about 1 g/l to about 20 g/l. of copper, with about 5.6 g/l being preferred. It is also possible to employ the composition of the present invention in a non-aquaous or "dry" form, in which case the ratio of quaternary ammonium compound or system to copper in the composition may range from about 0.5 to about 250, with a ratio of about 5.7 being preferred.

In the treatment of water in swimming pools employing, for example, sand filters working at high speed, a solution of quaternary ammonium compounds can have the effect of dispersing fine particles which are present in the water but which are not removed from the system by the filter. Under such circumstances, it is desirable to include a flocculating agent in the composition. The preferred such agent is an aluminum salt, such as aluminum chloride, compatible with quaternary ammonium compounds. The precipitate of aluminium species thus formed by the salt in the water unites and attracts suspended impurities. By combining the aluminium chloride with the two preceding constituents, i.e., quaternary ammonium system and copper salt, a dual action product is obtained. That is, the product has biocidal properties resulting from the quaternary ammonium system and the copper salt and flocculent properties derived from the aluminum salt. Aluminum chloride can be used as desired, preferably either as a solution of aluminum chloride having strength of approximately 12% of aluminum and 24% of chloride, which chloride is acidic; or as a basic aluminum chloride, the properties of which are as follows:

general formula: $Al_n (OH)_m (SO^4)_K Cl\ 3n\text{-}m\text{-}k$

Basicite $B = \frac{m}{3n} \times 100 = 40\ a\ 60$ $Al_2O_3$:10%; Cl:9.5%; $(SO_4)$:2.7%
Poids du litre: 1,200 Kg. (weight of liters)

Other compounds suitable for use as a flocculent in the biocide composition of the present invention include aluminum bromides and acetates, and other metals such as iron and zinc in the form of chlorides, bromides, acetates, and other solubilizing anions compatible with quaternary ammonium systems. One or more of such flocculents can be employed either in conjunction with aluminum chloride or in place of aluminum chloride. The flocculating agent, can be present in the composition in aqueous form in an amount ranging from 0 to approximately 50 g/l of $Al_2O_3$, with about 8.8 g/l of $Al_2O_3$ being preferred. In a "dry" composition, the ratio of flocculent to quaternary ammonium compound can range from 0 to about 5.0.

Optionally, any one or more of a group of additives may be included in the composition, such as perfumes, anti-foaming agents, colorants and insect repellants. Eucalyptus oil is the preferred additive serving as an anti-foaming agent and an insect repellant and can be present in the range of about 0 to about 21 per 2500 l of final product. However, since approximately 1.250 l per 2500 l final product is about the saturation point for eucalyptus oil in the final product, it is preferable not to add any more such oil than will go into solution.

EXAMPLE 1

With reference to FIG. 1, to manufacture the preferred composition of the present invention a solution of 565 kg of copper sulfate (containing 5.85% copper) is added with stirring to 715 kg of a solution of sodium carbonate (containing 9.2% sodium carbonates). At the end of this operation, 200 liters of water is added. The system 1 is stirred for a few additional minutes and then allowed to settle 2 for 12 to 24 hours. The solution 3 is then siphoned from any solid present in the system. 1300 liters of water are then added to the stirred solution 4. The system is then allowed to sit 5, and the solution 6 is again siphoned from any solid present in the system. 1300 liters of water are again added, the solution 7 stirred, allowed to settle 8 and then subsequently siphoned 9 from any solid material which is present. These operations are repeated as indicated at 10, 11 and 12 until the conductivity of the water is close to that of the water used for dilution. At this point, 1500 liters of water are added. The resulting solution 13 is stirred while slowly adding 72 kilograms of 99% acetic acid, 28 kg of 80% formic acid, 3.5 kg pure trichloracetic acid, followed by sufficient water necessary to obtain a total weight of 2100 kg containing 33 kg of copper.

Into the stirred, homogeneous solution 14 is added a solution of 400 kg of quaternary ammonium compounds having a strength of 50% of active material and 1,250 liters of eucalyptus oil. The purpose of the eucalyptus oil is to repel any insects and to decrease the foam.

The resulting product is a composition comprising the following constituents:

| Constituent | | | Weight % of total solution |
|---|---|---|---|
| (1) alkyl dimethyl benzyl ammonium chloride of the general structure: | | | 8.0% |
| | | $C_8$— | 0.24% |
| | $CH_3$ | $C_{10}$— | 0.48% |
| + | | $C_{12}$— | 4.70% |
| R—N | $CH_3$ Where R = | $C_{14}$— | 1.30% |
| | | $C_{16}$— | 0.64% |
| | $CH_2C_6H_5$ | $C_{18}$(stearyl)- | 0.12% |
| | Cl | $C_{18}$(oleyl)- | 0.40% |
| (2) copper salts from the group: cupric acetate, $C_4H_6CuO_4$ cupric formate, $C_2H_2CuO_4$ cupric trichloroacetate, $C_4HCl_3CuO_4$ | | | 1.31% |
| (3) Cineola/Eucalyptol, $C_{10}H_{18}O$ | | | 0.05% |
| (4) (Balance is water) | | | |

The quantities of acid indicated above correspond to the quantities required such that the pH of the manufactured product falls in the range 3.9 to 4. Instead of using the indicated copper salts, the commercial copper salts such as copper acetate or hydrocarbonate can be employed. However, for purity reasons, it is preferrable to use commercial sodium carbonate and commercial copper sulfate.

The resulting aqueous biocide solution composition works well for a number of uses, such as the cleaning of soil and the treatment of swimming pool water where flocculation is of no concern. It may also be used to disinfect animal breeding places by, for example, diluting 1 liter of the solution with 100 to 300 liters of waters and applying the resulting dilution to the walls and floors of buildings or places where animals are bred.

EXAMPLE 2

Where flocculation is desired, before preparing the dual action formula of the present invention, a flocculent solution is first prepared. The preferred flocculent solution is based on aluminum chloride, but is characterized by the presence of copper salts in order to give it algacidic power and, at the same time, to increase the weight of the precipitate aluminum species in order to facilitate its decantation. As indicated above either (a) an acidic, or (b) a basic solution of aluminum chloride may be used.

(a) Preparation of the acidic aluminum chloride solution:

To a stirred solution of 850 kg of chloride (containing 12% aluminum) is added enough hydrated copper hydrocarbonate to achieve 3,200 kg of copper (for instance, 11.8 kg or 27%) and a sufficient quantity of water to obtain 1000 kg. The systems is stirred until solution is complete. The acidic aluminum chloride solution thus obtained contains b 10% aluminum and 0.32% copper.

(b) Preparation of the basic aluminum chloride solution:

To a stirred solution of 850 kg of basic chloride (containing 10% $Al_2O_3$), is added a copper solution of 150 kg (containing 2.15% copper) which was prepared from the hydrocarbonate and acetic and formic acid, as above. The basic solution thus obtained contains of 8.5% aluminum and 0.32% copper.

To prepare the dual action composition of the present invention from the acidic aluminum chloride solution, 100 kg of the acidic aluminum chloride solution of Example 2(a) above and 480 kg of the biocide composition of Example 1 above containing the quaternary ammonium compounds are added, while stirring, to 620 kg of water, resulting in 1200 kg of dual action composition, having a density of 1.026, the strength of which is 32 g/l of quaternary ammoniums, 5.6 g/l of copper, and 8.8 g/l of alumina.

To prepare the composition of the present invention from the basic aluminum chloride solution, 3 kg of 80% formic acid, 120 kg of the basic aluminum chloride solution and 480 kg of the quaternary ammonium solution of Example 1 are added, while stirring, to 597 kg of water resulting in 1200 kg, the pH of which ranges the pH of which ranges between 3.7 and 4 (in general, 3.8–3.9). The content of quaternary ammoniums, copper and aluminum in the resulting solution is the same as the resulting solution prepared from the acidic aluminum chloride solution.

To treat swimming pool water, the application of about 4 Kg of the composition of Example 1 per 100 cubic meters of water when filling the pool, followed by about 1 Kg every two to three weeks has been found to be extremely effective in controlling the presence of micro-organisms in the water system. To obtain the same level of biocidal activity with the aid of quaternary ammonium compounds alone requires a concentration at least four times stronger than that provided by the preferred composition of the present invention, with the biocidal effect of the quaternary ammonium alone being much shorter. When used to treat water in swimming pools in doses of 10 to 20 liters per 100 cubic meters of the pool water, the dual action composition of the present invention furnishes 3.3 to 6.6 PPM of quaternary ammonium, 0.53 to 1.06 PPM copper, and 0.88 to 1.76 PPM alumina, per cubic meter of water.

EXAMPLE 3

To the biocide composition of Example 1 was added the orange colorant acridine with no effect on the biocidal acitivity of the composition.

In the foregoing specification, many specific embodiments and details as to specific compositions have been set forth. It will, however, be apparent to those skilled in the art that certain of the details thereof may be varied without departing from the spirit and scope of the present invention.

I claim:

1. An improved composition for treatment of swimming pool water consisting of biocide constituents and a flocculent in which the biocide constituents are a mixture of quaternary ammonium compounds and salts of copper wherein the mixture of quaternary ammonium compounds function as an algaecide, a bactericide, and a fungicide, and the copper salts function as an algaecide.

2. A method of treating water to control the growth of micro-organisms in said water comprising adding to the water about 3.3 to 6.6 PPM of a quaternary ammonium compound and about 0.53 to 1.06 PPM copper cation per cubic meter of said water to be treated.

3. The method of claim 2 further including adding about 0.88 to 1.76 PPM soluble aluminum species.

4. The water treatment composition of claim 1 in which the quaternary ammonium compounds and the salts of copper function in a synergistic manner.

5. The water treatment composition of claim 1 in which the flocculent is selected from the group of compounds containing aluminum, iron, or zinc compatible with the biocide constituents and mixtures thereof.

6. The water treatment composition of claim 1 further including a defoamer and insect repellant.

7. The water treatment composition of claim 6 in which the defoamer and insect repellent is cineola/eucalyptol.

8. The water treatment composition of claim 1 in which the quaternary ammonium compounds are chlorides or bromides of the following structures:

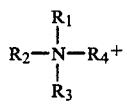

wherein $R_1$ is a long chain [$C_8$–$C_{20}$] aliphatic hydrocarbon and $R_2$, $R_3$ and $R_4$ are selected from the group consisting of methyl, ethyl, n-propyl, benzyl, and combinations thereof; or amphoteric compounds wherein $R_1$ is a long chain [$C_8$–$C_{20}$] aliphatic hydrocarbon, $R_2$ is either $-CH_2CO_2$, or $-CH_2-CH_2-CO_2$, and $R_3$ and $R_4$ are selected from the group consisting of methyl, ethyl, n-propyl, benzyl and combinations thereof.

9. The water treatment composition of claim 5 in which the aluminum, iron and zinc compounds are in the form of chlorides, bromides, acetates, or other solubilizing anions compatible with the biocide constituents.

10. The water treatment composition of claim 1 in which the copper salts are selected from the group consisting of chlorides, bromides, sulfates, acetates, formates, trichloroacetates, hydrocarbonates and other solubilizing anions compatible with the quaternary ammonium compounds and mixtures thereof.

11. A composition having improved biocide acitvity comprising a quaternary ammonium compound and a copper salt compatible with the quaternary ammonuim compound, said quaternary ammonium compound and said copper salt being present in the ratio of about 0.5 to about 250 quaternary ammonium compound to copper salt.

12. The composition of claim 11, wherein the quaternary ammonium compound is selected from the group consisting of chlorides and bromides of the following structure:

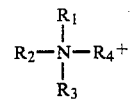

where $R_1$ is a long chain [$C_8$–$C_{20}$] aliphatic hydrocarbon and $R_2$, $R_3$ and $R_4$ are selected from the group consisting of methyl, ethyl, n-propyl, benzyl, and combinations thereof; amphoteric compounds where $R_1$ is a long chain [$C_8$–$C_{20}$] aliphatic hydrocarbon, $R_2$ is either $-CH_2CO_2-$, or $-CH_2-CH_2-CO_2$, and $R_3$ and $R_4$ are selected from the group consisting of methyl, ethyl, n-propyl, benzyl and combinations thereof; and mixtures thereof.

13. The composition of claim 11, wherein the copper salt is selected from the group consisting of chlorides, bromides, sulfates, acetates, formates, trichloroacetates, hydrocarbonates, and other solubilizing anions compatible with the quaternary ammonium compound.

14. The composition of claim 11, wherein the composition is an aqueous solution.

15. The composition of claim 11, further including a flocculent compatible with the quaternary ammonium compound and the copper salt.

16. The composition of claim 15, wherein the flocculent is selected from the group consisting of aluminum, iron and zinc chlorides, bromides, acetates and other solubilizing anions compatible with the composition.

17. The composition of claim 15, wherein the flocculent is present in the amount of from 0 to about 50 g/l.

18. The composition of claim 11, further including a defoamer and insect repellent compatible with the quaternary ammonium compound and the copper salt.

19. An aqueous composition, acting both as a biocide and as a flocculent, comprising:
a quaternary ammonium compound present in the amount of about 10 g/l to about 250 g/l;
a copper salt, compatible with the quaternary ammonium compound, present in the amount of about 1 g/l to about 20 g/l; and
a flocculent, compatible with both the quaternary ammonium compound and the copper salt, present in the amount of up to about 50 g/l.

20. The composition of claim 19, wherein the quaternary ammonium compound is selected from the group consisting of chlorides and bromides of the following structure:

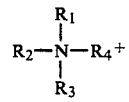

where $R_1$ is a long chain [$C_8$–$C_{20}$] aliphatic hydrocarbon and $R_2$, $R_3$ and $R_4$ are selected from the group consisting of methyl, ethyl, n-propyl, benzyl, and combinations thereof; amphoteric compounds wherein $R_1$ is a long chain [$C_8$–$C_{20}$] aliphatic hydrocarbon, $R_2$ is either $-CH_2CO_2-$, or $-CH_2-CH_2-CO_2$, and $R_3$ and $R_4$ are selected from the group consisting of methyl, ethyl, n-propyl, benzyl and combinations thereof; and mixtures thereof.

21. The composition of claim 19, wherein the copper salt is selected from the group consisting of chlorides, bromides, sulfates, acetates, formates, trichloroacetates, hydrocarbonates, and other solubilizing anions compatible with the quaternary ammonium compounds.

22. The composition of claim 19, further including a flocculent compatible with the quaternary ammonium compound and the copper salt.

23. The composition of claim 22, wherein the flocculent is selected from the group consisting of aluminum iron and zinc chlorides, bromides, acetates and other solubilizing anions compatible with the composition.

24. The composition of claim 19, further including an anti-foaming agent.

25. The composition of claim 24, wherein the anti-foaming agent is eucalytptus oil.

26. The method of claim 2, wherein the quaternary ammonium system is selected from the group consisting of chlorides and bromides of the following structure:

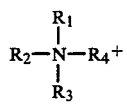

where $R_1$ is a long chain $[C_8–C_{20}]$ aliphatic hydrocarbon and $R_2$, $R_3$ and $R_4$ are selected from the group consisting of methyl, ethyl, n-propyl, benzyl, and combinations thereof; amphoteric compounds where $R_1$ is a long chain $[C_8–C_{20}]$ aliphatic hydrocarbon, $R_2$ is either $-CH_2CO_2-$, or $-CH_2-Ch_2-CH_2$, and $R_3$ and $R_4$ are selected from the group consisting of methyl, ethyl, n-propyl, benzyl and combinations thereof; and mixtures thereof.

27. The method of claim 2, wherein the copper cation is obtained from an aqueous copper salt solution including a copper salt selected from the group consisting of chlorides, bromides, sulfates, acetates, formates, trichloroacetates, hydrocarbonates, and other solubilizing anions compatible with the quaternary ammonium compound.

28. The method of claim 3, wherein the soluble aluminum species is obtained from an aqueous solution including aluminum compound selected from the group consisting of aluminum chlorides, bromides, acetates and other solubilizing anions compatible with the composition.

* * * * *